United States Patent
Neubauer et al.

(10) Patent No.: US 9,135,704 B2
(45) Date of Patent: Sep. 15, 2015

(54) SPATIAL AND SHAPE CHARACTERIZATION OF AN IMPLANTED DEVICE WITHIN AN OBJECT

(75) Inventors: Anne M. Neubauer, Denver, CO (US); Michael Grass, Buchholz in der Nordheide (DE); John D. Carroll, Littleton, CO (US); Shiuh-Yung J. Chen, Englewood, CO (US)

(73) Assignees: Koninklijke Philips N.V., Eindhoven (NL); The Regents of the University of Colorado, a body corporate, Denver, CO (US)

( * ) Notice: Subject to any disclaimer, the term of this patent is extended or adjusted under 35 U.S.C. 154(b) by 399 days.

(21) Appl. No.: 13/379,041

(22) PCT Filed: Jun. 17, 2010

(86) PCT No.: PCT/IB2010/052725
§ 371 (c)(1),
(2), (4) Date: Apr. 24, 2012

(87) PCT Pub. No.: WO2010/150147
PCT Pub. Date: Dec. 29, 2010

(65) Prior Publication Data
US 2012/0280980 A1    Nov. 8, 2012

Related U.S. Application Data

(60) Provisional application No. 61/219,918, filed on Jun. 24, 2009.

(51) Int. Cl.
*G06K 9/00* (2006.01)
*G06T 7/00* (2006.01)
(Continued)

(52) U.S. Cl.
CPC .............. *G06T 7/0014* (2013.01); *A61B 6/12* (2013.01); *G06T 17/00* (2013.01); *G06T 19/20* (2013.01);
(Continued)

(58) Field of Classification Search
USPC .................................. 382/128–134, 141–152
See application file for complete search history.

(56) References Cited

U.S. PATENT DOCUMENTS

| | | | |
|---|---|---|---|
| 5,741,327 A | 4/1998 | Frantzen | |
| 6,694,178 B1 | 2/2004 | Soula et al. | |
| 2004/0076316 A1* | 4/2004 | Fauci | 382/128 |
| 2004/0107403 A1 | 6/2004 | Tetzchner et al. | |
| 2006/0015934 A1 | 1/2006 | Wool | |
| 2006/0098855 A1* | 5/2006 | Gkanatsios et al. | 382/128 |
| 2006/0159341 A1* | 7/2006 | Pekar et al. | 382/173 |

(Continued)

FOREIGN PATENT DOCUMENTS

| | | | |
|---|---|---|---|
| JP | 2001076184 A | 3/2001 | |
| WO | 2004016182 A1 | 2/2004 | |

(Continued)

OTHER PUBLICATIONS

Ioannis Kompatsiaris et al, "Deformable Boundary Detection of Stents in Angiographic Images", IEEE Transactions on Medical Imaging, IEEE Service Center, Piscataway, NJ, US, vol. 19, No. 6, Jun. 1, 2000, XP011035990, ISSN: 0278-0062.

*Primary Examiner* — Alex Liew

(57) ABSTRACT

It is described a method for spatially characterizing a device positioned within an object, e.g. a patient's body, under examination that e.g. allows a clinician to easily assess the deployment state and position of the device. The method comprises the steps of acquiring (26) a set of images of the device, reconstructing (28) a three-dimensional model of the device from the set of images, comparing (30) the model of the device with an ideal model of the device in a predetermined deployment state inside the object and displaying (36) the model of the device on a display unit. For optical indication deviation areas of the deployed device relative to an ideal model of the deployed device can be determined and color-coded depending on the strength of deviation.

10 Claims, 3 Drawing Sheets

(51) Int. Cl.
   *A61B 6/12*    (2006.01)
   *G09B 23/28*   (2006.01)
   *G06T 17/00*   (2006.01)
   *G06T 19/20*   (2011.01)

(52) U.S. Cl.
   CPC ............ *G09B 23/28* (2013.01); *G06T 2200/04* (2013.01); *G06T 2207/10116* (2013.01); *G06T 2207/30048* (2013.01); *G06T 2210/21* (2013.01); *G06T 2210/41* (2013.01); *G06T 2219/2012* (2013.01)

(56) References Cited

U.S. PATENT DOCUMENTS

2008/0137923 A1*  6/2008  Spahn .................. 382/128
2008/0292149 A1   11/2008 Rasche

FOREIGN PATENT DOCUMENTS

| WO | 2004051572 A2 | 6/2004 |
| WO | 2006003576 A2 | 1/2006 |
| WO | 2008041154 A2 | 4/2008 |

* cited by examiner

SPATIAL AND SHAPE CHARACTERIZATION OF AN IMPLANTED DEVICE WITHIN AN OBJECT

FIELD OF INVENTION

The present invention relates to the field of digital image processing, in particular for medical purposes in order to provide a method for characterizing a device inserted into the body of a patient.

Specifically, the present invention relates to a method for spatially characterizing a device positioned within an object under examination.

Further, the present invention relates to a data processing device and to a medical X-ray examination apparatus.

Furthermore, the present invention relates to a computer-readable medium and to a program element having instructions for controlling the above-mentioned method for spatially characterizing a device positioned within an object under examination.

BACKGROUND OF THE INVENTION

In an increasing number of coronary and structural heart disease interventional procedures, percutaneous devices, for example stents, are placed and deployed in coronary arteries. These devices, which are collapsed onto a catheter for delivery, must be precisely sized and positioned for deployment during the procedure and often require evaluation afterwards. Once these devices are deployed into their final complex three-dimensional structure, the evaluation process is often subjective and non-standardized, such that tracking any clinical outcomes related to the position, sizing, or final shape of the structure can be difficult.

Evaluation of percutaneous devices directly after deployment or over longer time periods is currently accomplished only via visual inspection of 2D images acquired by X-ray examination apparatuses or by other imaging modalities, e.g. echocardiography. However, many of these devices have complex 3D shapes that are both difficult to assess using conventional projection-based imaging and which may change their shape in a way that is hard to discern with the eye alone. As more of these devices are being developed and require clinical evaluation for short- and long-term safety and efficacy, more advanced methods for determining their proper deployment and positioning over time may be required.

In WO 2008/041154 A2 a spatial characterization of a structure located within an object by identifying 2D representations of the structure within section planes is shown. There, a virtual pullback as a visualization and quantification tool that allows an interventional cardiologist to easily assess stent expansion is described. The virtual pullback visualizes the stent and/or the vessel lumen similar to an intravascular ultrasound pullback. The virtual pullback is performed in volumetric data along a reference line. The volumetric data can be a reconstruction of rotational 2D X-ray attenuation data. Planes perpendicular to the reference line are visualized as the position along the reference line changes. In these perpendicular section planes automatic measurement are calculated and displayed.

SUMMARY OF THE INVENTION

The success and accuracy of the assessment of the correct placement and deployment of percutaneous devices depend heavily on the experience of the clinician as well as on unambiguous 2D images from the device and the complexity of the device. However, if the device has a rather complex shape, the 2D images induce uncertainties and if the clinician is not experienced in assessing the deployment state of a particular percutaneous device, known methods for evaluation of placement and deployment of the percutaneous device need to be improved.

Accordingly, there may be a need for a method for characterizing a device positioned within an object under examination which may overcome at least some of the above insufficiencies. Particularly, there may be a need for a method for characterizing a device positioned within an object under examination that provides an accurate and unambiguous characterization of a device positioned within an object under examination, in particular in a body of a patient.

These needs may be met by the subject matter according to the independent claims. Advantageous embodiments of the present invention are described in the dependent claims.

According to a first aspect of the present invention, a method for spatially characterizing a device positioned within an object under examination is provided. The described method comprises a number of steps. In a first step a set of images is acquired in which the device of interest is made visible. The acquisition of this set of images can be realized by a number of different image acquisition methods, for example conventional two-dimensional X-ray images acquired under different viewing angles relative to the device. Therefore it may be beneficial to use an X-ray system comprising a C-arm and acquire a set of images during a rotational sweep of this C-arm.

In a subsequent step a three-dimensional model of the device is reconstructed using a variety of methods already in existence from the acquired set of images. There exist a variety of methods for reconstructing a three dimensional model from a set of images with different viewing angles, such as the standard filtered back-projection reconstruction for non-cardiac devices, or gated reconstruction or 3D device boosting in the case of cardiac devices. The expression "model" stands for the mathematical representation of the essential aspects of the devices' three dimensional shape which presents knowledge of that device in usable form, in terms of processability.

Afterwards, this reconstructed three-dimensional model is compared to an ideal model with an ideal deployment state for the related purpose and positioned in a predetermined position inside the object to be examined as following. After positioning and deploying the actual device in the object to be examined, e.g. a patient, the physician performs a rotational acquisition of the device. By using existing technology the device is reconstructed with high spatial resolution into a three-dimensional volume. The model of the ideal device would be fit to the actual device using template matching or other methods. Then, measurement of the difference between the deployed device and the ideal model of the device can be carried out after matching.

In case a percutaneous device, such as a stent, is to be spatially reconstructed, deviations relative to a desired stent expansion may be calculated. The stent expansion may be characterized by a maximum diameter of the cross sectional surface of the stent, depending on the desired vessel diameter.

It is clear that prior to this procedure a three-dimensional model of the ideally deployed device is required. This can be either obtained from the supplier of the device itself or through imaging studies of the device in vitro. This may be either a single model, since the ideally deployed shape may always be the same or a multitude of models, e.g. if the deployed shape depending on the pressure of the balloon used during deployment in using stents.

During the comparison of the three-dimensional representation of the actual device to the ideal structure of the deployed device areas of deviation may be calculated. Thereby color codes may be generated for representing the deviations between the model of the actual device and the ideal model with predetermined deployment state and position. Areas of large deviation or deformation from the ideal model would be color-coded to alert the physician to potential mis-positioning or under-deployment.

This first aspect of the present invention is based on the idea that e.g. a clinician or other person may be supported in positioning and deploying of a device in e.g. a patient's body in order to ensure that the device is deployed correctly. It is cumbersome to determine whether a device is positioned and deployed correctly using standard methods that are known in prior art. By using the method according to the present invention this determination is rather easy to accomplish. Furthermore, it is also rather easy to check the position and deployment state of a device after some time during regular medical examinations or the such.

According to an advantageous embodiment of the present invention, the reconstructed model is displayed on a display unit which may for example be a screen visible to the physician during an intervention process. Color codes generated to mark deviation areas can be applied to the displayed images in that the deviation areas have a different color than the remaining parts of the actual device. This helps the physician to easily recognize the areas where re-deployment or re-positioning of the device needs to be accomplished. As an example areas of heavy deviations in the shape of a percutaneous device may be marked red whereby other areas of only minor deviations may be marked green. It is clear that this list is not exhaustive and other color codes may be used for this purpose as well.

In a further embodiment of the present invention, the model of the device reconstructed at the time of original implantation may be compared with a model of the device from a later follow-up reconstruction using the same methodology to calculate deviation areas where the shape of the device or the actual position has changed. Thereby it can be assessed, whether the deployed percutaneous device has altered its shape or its position. This allows to evaluate the recent state of the device and to assess whether further interventions are necessary.

According to a further exemplary embodiment of the present invention the ideal model is displayed parallely to the reconstructed model of the actual deployed device. This may be in a temporary or a permanent manner.

The expression "temporary" stands for depicting the ideal model in a non permanent fashion, for example only for a given time upon pressing a dedicated button, a dial or a switch or conducting a appropriate command via a user interface. This may help in render the actual deviations more clear in that not only color codes may be used but also a visual comparison between the actual device and the ideal device is made easy.

Also, a permanent display of the ideal device model may be realised wherein the model may be displayed as an overlay over the reconstructed model of the actual device in a shaded/transparent manner, so that circumferences, outlines, contours of the ideal device may be recognized without disturbing the view of the reconstructed model of the actual device and vice-versa. The ideal model of the device could also be projected onto any 2D angiogram of the implanted device to check for similarities and differences.

Alternately, in another exemplary embodiment of the present invention the ideal model may be displayed in an alternate manner to the reconstructed model of the actual device, so that for example by triggering an input device the display unit switches between the actual device and the ideal model of the device. Thereby it may be very helpful to fit the position of the ideal model with the position of the actual device in order to easily recognize deformation deviations by flipping between the displays of the actual device model and the ideal model. In an ideal case only the outlines of these two models are different from each other so that by flipping between these two display options only the outlines of the two models flip between two neighbouring shapes.

Basically, the evaluation of the shapes difference between the implanted device and the ideal model may require two major processes. The ideal model is characterized by a surface-based parametric function $S_M(u, v)$, $0 \leq u, v \leq 1$, where u, v are the parametric variables. Similarly, the surface-based function of implanted device will be derived from the reconstructed volumetric data and is defined as $S_O(u',v')$, $0 \leq u', v' \leq 1$, where u',v' denote the parametric variables. The registration process may be employed such that the root-mean-square ("RMS") distance of pre-determined IV landmarks between the implanted device and ideal model will be the minimum based on the surface-based functions $S_M(u_i,v_i)$ and $S_O(u'_i,v'_i)$, i=1, 2, . . . N. After the registration process, the new surface-based function $\hat{S}_O(u, v)$ for the implanted device may be derived. For each surface point on the implanted device $\hat{S}_O(u, v)$, the nearest distance to the surface of ideal model $S_M(u, v)$ may be calculated and the calculated location at the ideal surface model is identified as the corresponding point. The resultant distances may then be color coded to represent the magnitude of shape change of implanted device with respect to the shape of ideal model.

According to a further aspect of the present invention there is provided a data processing device for spatially characterizing a device located within an object under examination. The data processing device preferably comprises a data processor, which is adapted for performing exemplary embodiments of the above-described method and preferably a memory for storing the acquired set of images of the device under examination, for the reconstructed model of the actual device and for the ideal model of the device. The model or type of data processing device is not relevant for successfully conducting the method according to the present invention.

According to further aspect of the present invention there is provided a medical X-ray examination apparatus, in particular a C-arm system or a computer tomography system. The medical X-ray examination apparatus comprises the above-described data processing device.

According to a further aspect of the present invention there is provided a computer-readable medium on which there is stored a computer program for spatially characterizing a device located within an object under examination. The computer program, when being executed by a data processor, is adapted for controlling exemplary embodiments of the above-described method.

According to a still further aspect of the present invention there is provided a program element for spatially characterizing a device located within an object under examination. The program element, when being executed by a data processor, is adapted for controlling exemplary embodiments of the above-described method.

The computer program element may be implemented as a computer-readable instruction code in any suitable programming language, such as, for example JAVA, C++ and may be stored on a computer-readable medium (removable disk, volatile or non-volatile memory, embedded memory etc.).

The instruction code is operable to program a computer or other programmable device to carry out the intended functions. The computer program may be available from a network, such as the WorldWideWeb, from which it may be downloaded.

Also, existing medical viewing systems may be upgraded with a new software, which, when being executed on a processor, causes the system to carry out the above-mentioned method steps according to the present invention.

It has to be noted that features and side effects of the present invention have been described with reference to different embodiments of the invention. However, a person skilled in the art will gather from the above and the following description that unless other notified in addition to any combination or features belonging to one embodiment also any combinations between features relating to different embodiments or to a manufacturing method is considered to be disclosed with this application.

The aspects defined above and further aspects of the present invention are apparent from the examples of embodiment to be described hereinafter and are explained with reference to the examples of embodiment. The invention will be described in more detail hereinafter for further explanation and better understanding of the present invention with reference to examples of embodiment but to which the invention is not limited. Identical or similar components in different figures are provided with identical reference numerals. The illustrations in the figures are schematic and are not to scale.

DETAILED DESCRIPTION OF EMBODIMENTS

Figure 1:
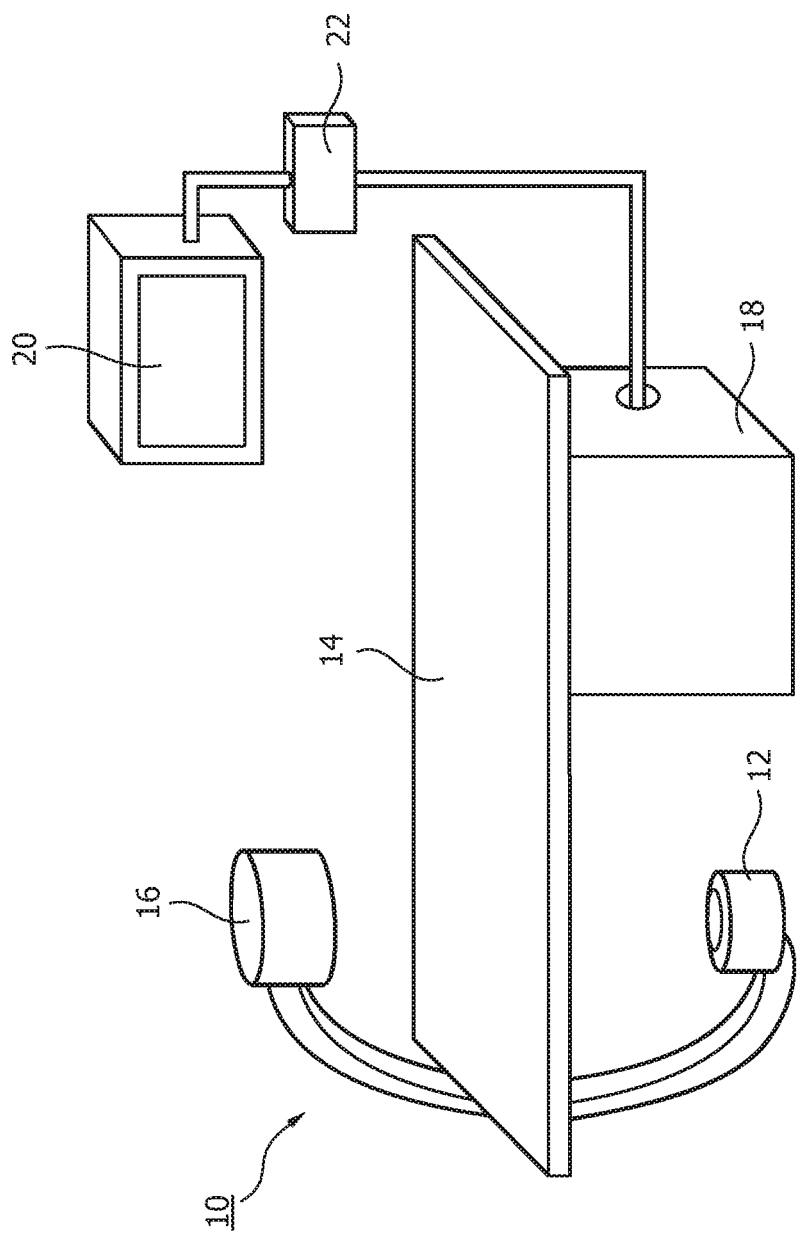
FIG. 1 shows an X-ray imaging system with an integrated viewing system for spatial characterizing of a device within an object under examination.

FIG. 1 schematically shows an X-ray imaging system 10 with a medical viewing system for spatial characterization of a device within an object under examination.

The X-ray imaging system 10 comprises an X-ray image acquisition device with a source of X-ray radiation 12 provided to generate X-ray radiation. A table 14 is provided to receive an object to be examined. Further an X-ray image detection module 16 is located opposite the source of X-ray radiation 12. During the radiation procedure, the examined object is located between the source of X-ray radiation 12 and the detection module 16. The latter sends data to a data processing unit or a calculation unit 18, which is connected to both the X-ray image detection module 16 and the X-ray radiation source 12. The calculation unit 18 is exemplary located underneath the table 14 for saving space within the examination room. It is clear that it could also be located at a different place, such as in a different room or a different laboratory. Furthermore, a display unit 20 is arranged in the vicinity of the table 14 for displaying information to the person operating the X-ray imaging system, which can be a clinician such as a cardiologist or cardiac surgeon. Preferably, the display unit 20 is movably mounted to allow for an individual adjustment depending on the examination situation. Also, an interface unit 22 is arranged to input information by the user.

Basically, the image detection module 16 generates images by exposing this subject to X-ray radiation, wherein said images are further processed in the calculation unit 18. It is noted that the example shown is of a so-called C-type X-ray image acquisition device. The X-ray image acquisition device comprises an arm in form of a C where the image detection module 16 is arranged at one end of the C-arm and the source of X-ray radiation 12 is located at the opposite end of the C-arm. The C-arm is movably mounted and can be rotated around the object of interest located on the table 14. In other words, it is possible to acquire images with different directions of view.

The calculation unit 18 may be adapted to conduct the method according to the present invention and thus can be considered as or comprise the data processing device for spatially characterizing a device located within an object under examination. Thereby, a data processor and preferably a memory for storing the acquired set of images is provided as well as a related software that with at least one program element for spatially characterizing a device located within an object under examination, adapted for controlling exemplary embodiments of the above-described method. The software can be transferred into the calculation unit 18 by means of a computer-readable medium or through a network and may be realised as a complete new operating system or an update.

Figure 2:
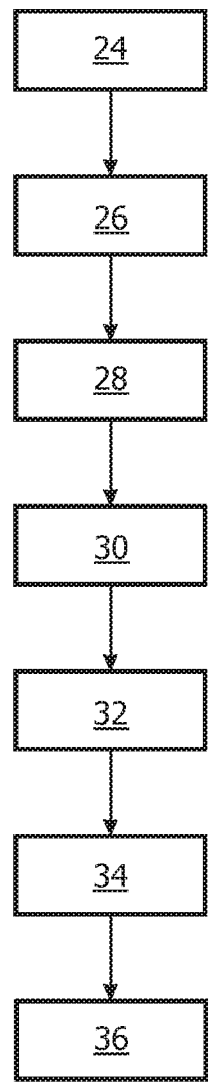
FIG. 2 shows a method for spatially characterizing a device within an object under examination.

The method according to the present invention is further described in FIG. 2 by way of a block diagram.

Firstly, a method step of obtaining 24 an ideal model of the device is given. This can either be realised by obtaining a model from the supplier of the related device or through separate imaging studies of the device in vitro. Without having this ideal model with a predetermined optimal shape in a deployed and positioned state the method according to the present invention can not be accomplished successfully. As described further above, this ideal model is not necessarily limited to a single model of the ideal device, it can also comprise a multitude of models that vary from each other depending on relevant deployment states e.g. pressure of a stent deployment balloon etc.

Further, a set of images of the actual device is acquired 26. The acquisition may preferably be accomplished by means of a common C-arm type X-ray examination apparatus shown in FIG. 1. Nevertheless, also other means for acquiring images may be utilized. Preferably, the acquired set of images contains images from the actual device positioned and deployed in the object to be examined that are acquired under different angles of view by rotating the C-arm of the X-ray examination apparatus.

Hereinafter, a model of the actual device is reconstructed 28 with high spatial resolution into three dimensional volume data using existing technology. Thereby, a three dimensional model from a set of images with different viewing angles, such as the standard 3DRA reconstruction for non-cardiac devices, or gated reconstruction or 3D device boosting in the case of cardiac devices is determined.

In a further step, the model of the actual device is compared 30 to the ideal model or one of the set of ideal models. Comparing 30 for example means fitting the model of the actual device with the ideal model in order to be able of determining shape deviations between these two models. Determined 32 deviations may be further processed in order to make them clearly visible to support the clinician.

In an exemplary embodiment of the present invention color codes are generated 34 that reflect the strength of deviations between these two models.

In a further exemplary embodiment of the present invention the ideal model and/or the actual model is displayed 36 on the display unit 20. Deviation areas between these two models may also be displayed wherein colors generated through the color codes are superposed 38, e.g. signaling colors like red or orange to mark stronger deviations and green for only minor deviations. Displaying 36 the ideal or actual model may be realised in an alternating manner, simultaneously or by selection.

The method according to the present invention gives a clinician the opportunity to accurately assess whether a deployed percutaneous device is positioned correctly and is also deployed to the desired shape. Deviations in the deployed shape are easily recognisable, so that the clinician may easily repeat the deployment process and bring the device, e.g. a stent or another percutaneous device to a correct deployment state.

Figure 3A:
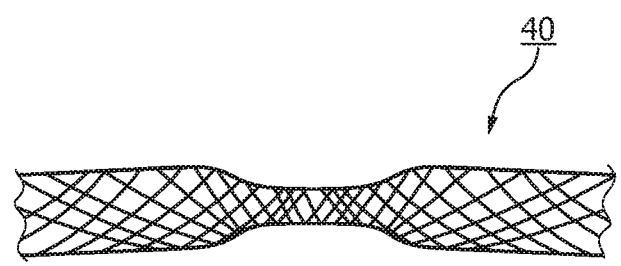
FIGS. 3a and 3b show an exemplary visualization of shape deviations of a device within an object under examination.

Further, in FIG. 3a a three-dimensional model of a stent 40 as an exemplary device to be deployed in a patient's body is shown as it may be displayed on a screen unit. While a clinician can visually determine where deviation areas exist using the 2D angiograms, an improved visualization method could potentially make this process faster, easier, and more accurate. Therefore, the actual model is compared with an ideal model in order to calculate deviation areas. These may be color coded so that deviation areas of the actual model may be colored on the screen unit appropriately.

Figure 3B:
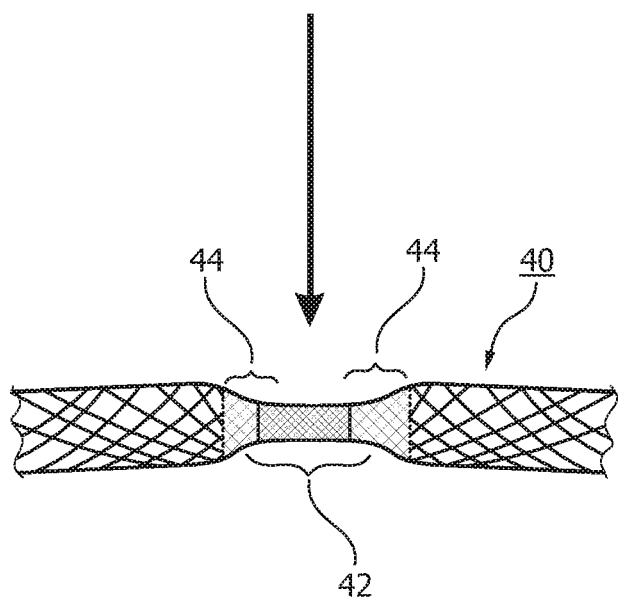

A colored actual model of the stent 40 is displayed in FIG. 3b. It is easily recognisable that a heavy contraction 42 exists in the middle part. It is obvious, that this shape is not the desired shape of the device. Therefore, the colors of this contraction 42 is chosen to illustrate the strength of deformation or deviation. Since the deviation considering the optimal shape is rather high, the contraction 42 is color coded red (dark pattern in FIG. 3b). Neighbouring areas 44 of the contraction 42 may be color coded green (light pattern) since their deviation is not as strong as at the contraction 42.

It is noted that this invention is not limited to the assessment of deployment states of stens. It may be utilised in a wide field of interventional operations, wherein the most direct application of this invention lies in the field of interventional cardiology, specifically for interventions involving devices such as septal defect repair devices, annuloplasty devices, among stents and others.

LIST OF REFERENCE SIGNS

10 X-ray imaging system
12 source of X-ray radiation
14 table
16 detection module
18 calculation unit
20 display unit
22 interface unit
24 obtaining ideal model
26 acquiring set of images
28 reconstructing model of actual device
30 comparing models
32 determining shape deviations
34 generating color codes
36 displaying
38 superposing colors
40 stent
42 contraction
44 neighbouring areas of contraction

The invention claimed is:

1. A method for spatially characterizing a device positioned and deployed within an object under examination, the method comprising the steps of
    acquiring a set of images of the device,
    reconstructing a three-dimensional model of the deployed device from the set of images,
    comparing the model of the deployed device with an ideal model of the device in a predetermined deployment state inside the object,
    displaying the model of the deployed device on a display unit;
    wherein the step of comparing comprises determining deviation areas in shape of the mode of the deployed device compared to the ideal model; and
    wherein the step of displaying comprises visualizing the deviation areas.

2. The method according to claim 1, further comprising the step of generating color-codes depending on a strength of deviation of the deviation areas and superposing colors according to the generated color-codes onto the displayed model of the deployed device on the display unit.

3. The method according to claim 1, further comprising the step of temporarily displaying the ideal model.

4. The method according to claim 3, wherein the ideal model is displayed as an overlay to the reconstructed model of the actual deployed device in a partially transparent manner.

5. The method according to claim 3, wherein the ideal model is displayed alternately to the reconstructed model of the actual deployed device.

6. The method according to claim 4, wherein the ideal model is displayed repeatedly.

7. The method according to claim 1, wherein the ideal model is displayed as an overlay to a 2D angiogram of the actual deployed device to check for differences and similarities.

8. A data processing device for spatially characterizing a device positioned within an object under examination, the data processing device comprising a data processor, which is adapted for performing the method as set forth in claim 1, and
    a memory for storing the acquired images and/or for storing the three-dimensional model of the deployed device.

9. A medical X-ray examination apparatus comprising a data processing device according to claim 7.

10. A computer-readable non-transitory storage medium on which there is stored a computer program for spatially characterizing a device positioned within an object under examination,
    the computer program, when being executed by a data processor, is adapted for controlling the method as set forth in claim 1.

* * * * *